United States Patent
Weingärtner et al.

(10) Patent No.: US 10,531,812 B2
(45) Date of Patent: Jan. 14, 2020

(54) SYSTEM AND METHOD FOR IMPROVED CARDIAC IMAGING OF SUBJECTS WITH ADVERSE CARDIAC CONDITIONS

(71) Applicants: Sebastian Weingärtner, Heidelberg (DE); Mehmet Akçakaya, Cambridge, MA (US); Warren J. Manning, Natick, MA (US); Reza Nezafat, Newton, MA (US)

(72) Inventors: Sebastian Weingärtner, Heidelberg (DE); Mehmet Akçakaya, Cambridge, MA (US); Warren J. Manning, Natick, MA (US); Reza Nezafat, Newton, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 93 days.

(21) Appl. No.: 13/742,620

(22) Filed: Jan. 16, 2013

(65) Prior Publication Data
US 2014/0200436 A1 Jul. 17, 2014

(51) Int. Cl.
*A61B 5/055* (2006.01)
*G01R 33/56* (2006.01)
(Continued)

(52) U.S. Cl.
CPC .................................. *A61B 5/055* (2013.01)

(58) Field of Classification Search
None
See application file for complete search history.

(56) References Cited

U.S. PATENT DOCUMENTS 6,219,571 B1 * 4/2001 Hargreaves et al. ......... 600/410
7,561,909 B1 * 7/2009 Pai .......................... A61B 5/055
324/307
(Continued)

FOREIGN PATENT DOCUMENTS

CN 102018511 A 4/2011
JP 2005278919 A 10/2005
(Continued)

OTHER PUBLICATIONS

Chow, et al., T2-dependent Errors in MOLLI T1 Values: Simulations, Phantoms, and In-Vivo Studies, Journal of Cardiovascular Magnetic Resonance, 2012, 14(Suppl 1):P281, 2 pages.
(Continued)

*Primary Examiner* — Thomas J Hong
*Assistant Examiner* — Shahdeep Mohammed
(74) *Attorney, Agent, or Firm* — Quarles & Brady LLP (57) ABSTRACT

A system and method for controlling a magnetic resonance imaging (MRI) system to acquire images of a subject having inconsistencies in a cardiac cycle of the subject. The process includes receiving an identification of a predetermined point in a cardiac cycle of the subject and, thereupon, performing a saturation module configured to dephase magnetization within a region of interest (ROI) from before the predetermined point. The process also includes performing an inversion module configured to invert spins within the ROI and acquiring medical imaging data from the subject. A delay is inserted between the performance of the saturation module and the performance of the inversion module, wherein a duration of the delay is configured, with the saturation module, to control evidence in the medical imaging data of inconsistencies in the cardiac cycle of the subject by controlling a magnetization history of tissue in the ROI.

20 Claims, 3 Drawing Sheets

(51) Int. Cl.
  *A61B 5/00* (2006.01)
  *G01R 33/50* (2006.01)
  *G01R 33/567* (2006.01)

(56) References Cited

U.S. PATENT DOCUMENTS

| | | | |
|---|---|---|---|
| 2008/0081986 A1* | 4/2008 | Slavin | 600/410 |
| 2009/0005673 A1 | 1/2009 | Rehwald et al. | |
| 2010/0219829 A1 | 9/2010 | Rehwald et al. | |
| 2012/0179028 A1* | 7/2012 | Caravan et al. | 600/420 |
| 2012/0194187 A1* | 8/2012 | Rehwald | G01R 33/5602 324/309 |
| 2013/0274592 A1* | 10/2013 | Shin et al. | 600/420 |

FOREIGN PATENT DOCUMENTS

| | | |
|---|---|---|
| JP | 2008086343 A | 4/2008 |
| JP | 2011092678 A | 5/2011 |

OTHER PUBLICATIONS

Cooper, et al., Flip Angle Profile Correction for T1 and T2 Quantification with Look-Locker Inversion Recovery 2D Steady-State Free Precession Imaging, Magnetic Resonance in Medicine, 2012, 68:1579-1585.

Deichmann, et al., Quantification of T1 Values by Snapshot-Flash NMR Imaging, Journal of Magnetic Resonance, 1992, 96:608-612.

Kim, et al., The Use of Contrast-Enhanced Magnetic Resonance Imaging to Identify Reversible Myocardial Dysfunction, New England Journal of Medicine, 2000, 343:1445-1453.

Kim, et al., How We Perform Delayed Enhancement Imaging, Journal of Cardiovascular Magnetic Resonance, 2003, 5(3):505-514.

Look, et al., Time Saving in Measurement of NMR and EPR Relaxation Times, Review of Scientific Instruments, 1970, 41(2):250-251.

Messroghli, et al., Modified Look-Locker Inversion Recovery (MOLLI) for High-Resolution T1 Mapping of the Heart, Magnetic Resonance in Medicine, 2004, 52(1):141-146.

Peters, et al., Detection of Pulmonary Vein and Left Atrial Scar After Catheter Ablation with Three-Dimensional Navigator-Gated Delayed Enhancement MR Imaging: Initial Experience, Radiology, 2007, 243(3):690-695.

Song, et al., Flexible Cardiac T1 Mapping Using a Modified Look-Locker Acquisition with Saturation Recovery, Magnetic Resonance in Medicine, 2012, 67:622-627.

PCT International Search Report and Written Opinion, PCT/US2014/011287, dated Jun. 18, 2014.

* cited by examiner

SYSTEM AND METHOD FOR IMPROVED CARDIAC IMAGING OF SUBJECTS WITH ADVERSE CARDIAC CONDITIONS

GOVERNMENT SUPPORT

This invention was made with government support under EB008743 awarded by the National Institutes of Health. The government has certain rights in the invention.

BACKGROUND OF THE INVENTION

The field of the invention is systems and methods for magnetic resonance imaging (MRI). More particularly, the invention relates to systems and methods for imaging subject with arrhythmia, heart rate variability, and other adverse cardiac conditions.

When a substance such as human tissue is subjected to a uniform magnetic field (polarizing field $B_0$), the individual magnetic moments of the nuclear spins in the tissue attempt to align with this polarizing field, but precess about it in random order at their characteristic Larmor frequency. Usually the nuclear spins are comprised of hydrogen atoms, but other NMR active nuclei are occasionally used. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$; also referred to as the radiofrequency (RF) field) which is in the x-y plane and which is near the Larmor frequency, the net aligned moment, $M_z$, may be rotated, or "tipped" into the x-y plane to produce a net transverse magnetic moment $M_t$, which is rotating, or spinning, in the x-y plane at the Larmor frequency. The practical value of this phenomenon resides in the signal which is emitted by the excited spins after the excitation field $B_1$ is terminated. There are a wide variety of measurement sequences in which this nuclear magnetic resonance (NMR) phenomenon is exploited.

When utilizing these signals to produce images, magnetic field gradients ($G_x$, $G_y$, and $G_z$) are employed. Typically, the region to be imaged experiences a sequence of measurement cycles in which these gradients vary according to the particular localization method being used. The emitted MR signals are detected using a receiver coil. The MRI signals are then digitized and processed to reconstruct the image using one of many well-known reconstruction techniques.

One common clinical application for MRI is cardiac and cardiovascular imaging. Late Gadolinium Enhancement (LGE) is the current gold standard for evaluation of scar and fibrosis in ischemic and non-ischemic patients. The role of LGE in the assessment of patients with ischemic cardiomyopathy has been extensively studied. LGE imaging has also been used for imaging of scar in left atrium and pulmonary veins in patients with atrial fibrillation (AF) (the most common cardiac arrhythmia prevalent in the elderly), in patients with hypertension, and in patients with coronary artery disease (CAD). Two-dimensional (2D) imaging studies are typically used clinically for LGE imaging. Three dimensional (3D) imaging has been introduced as an alternative approach for assessment of scar, which provides better volumetric coverage and higher signal-to-noise-ratio (SNR) than 2D imaging. However, 3D acquisitions take longer to complete and, thus, are more taxing on the patient. While 2D images can be acquired within a short breathhold of 10-15 seconds, 3D images are often 5-10 minutes in duration and, thus, require free-breathing.

In practice, LGE images are acquired after administration of a gadolinium contrast agent using a T1-weighted inversion recovery pulse sequence. The inversion time is selected prior to performing the LGE sequence using a Look-Locker imaging sequence such that the healthy myocardium signal is nulled. Abnormal washout kinetics in infarcted tissue enables the depiction of scar as bright regions against a dark myocardial background. Assuming a constant inversion time throughout the entire scan, the time between two inversion pulses in LGE imaging is preferably selected to equal the duration of the previous heartbeat, such that the heart is in a common portion of the cardiac phase during each successive acquisition. Failure to time the acquisition properly will result in substantial artifacts in the resulting images and will degrade the clinical utility of the images. Unfortunately, while this timing is necessary to avoid serious motion artifacts this time (typically 750-1000 ms) is too short to allow full recovery of the longitudinal magnetization of the cardiac tissue and most of the surrounding structures. Hence, the LGE signal is directly influenced by the length of the previous R-R interval.

This process is further complicated if the heart rate is inconsistent or variable and/or an arrhythmia is present. Such variability will cause a time-varying weighting of k-space lines, which results in ghosting artifacts. Therefore, arrhythmia and heart rate variability are among major factors that could deteriorate image quality, particularly, when performing a 3D LGE imaging study, which requires relatively long scan times.

While LGE is routinely utilized for the detection of large, localized scar areas, its use in detecting diffuse fibrosis is limited, even in sinus rhythm. Myocardial T1 mapping recently emerged as a supplementary sequence in the detection of scar and fibrosis. Due to its quantitative nature, T1 mapping allows for inter- and intra-patient reproducibility, and may facilitate the diagnosis of diffuse fibrosis in the myocardium. However, due to cardiac and respiratory motion, myocardial T1 mapping remains a challenging task.

Recently, the modified Look-Locker inversion recovery (MOLLI) sequence was proposed in Messroghli D R, Radjenovic A, Kozerke S, Higgins D M, Sivananthan M U, Ridgway J P, *Modified Look-Locker inversion recovery (MOLLI) for high-resolution T1 mapping of the heart.* Magnetic Resonance in Medicine 2004;52(1):141-146, for cardiac T1 mapping, and has been used in clinical and pre-clinical trials. By performing three-to-five data readouts after each preparation pulse, MOLLI incorporates the efficient sampling of the spin-lattice relaxation curve that was originally proposed in Look D C, Locker D R. *Time saving in measurement of NMR and EPR relaxation times,* Review of Scientific Instruments 1970;41(2):250-251. In order to provide a sufficient number of sampling points of the curve, three groups of images are acquired, each following a single inversion pulse. The three groups contain 3, 3, and 5 ECG-triggered images, respectively, which are acquired in consecutive heartbeats. Two rest periods of multiple heart cycles each separate these three groups in order to allow for sufficient recovery of the longitudinal magnetization. These rest cycles decrease the imaging efficiency and require relatively long breath holds, for example, 17 heartbeats. Furthermore, a fixed set of sample points on the T1 relaxation curve is predetermined by the ECG triggering, which impacts the T1 calculation, resulting in poor fit conditions for short T1 times. Furthermore, the signal disturbance of the relaxation curve induced by imaging varies based on the heart rate. For long T1 times, this results in a pronounced heart rate dependence of the calculated T1 values.

Thus, it would be desirable to have a system and method for an improved magnetization preparation technique to enable assessment of scar and diffuse fibrosis in the presence of arrhythmia or heart rate variability.

SUMMARY OF THE INVENTION

The present invention overcomes the aforementioned drawbacks by providing a system and method for imaging that utilizes a saturation pulse added at the beginning of each heartbeat, followed by an inversion pulse after a variable delay. The saturation pulse dephases the magnetization from the previous heartbeat and the inversion pulse generates improved contrast in the T1-weighted image. The utilization of the saturation preparation removes the sensitivity to heart-rate variability or arrhythmia in LGE imaging and possibly other T1 weighted cardiac imaging protocols by "erasing" magnetization history. Additionally, in T1 mapping, the saturation preparation eliminates the need for recovery periods, and allows the acquisition of one data readout per inversion, thus, improving imaging efficiency. Furthermore, it enables freedom to choose the distribution of the sampling points of the relaxation curve providing higher flexibility in T1 mapping.

In accordance with one aspect of the present invention, a method for controlling a magnetic resonance imaging (MRI) system using a pulse sequence to acquire images of a subject having inconsistencies in a cardiac cycle of the subject is disclosed. The method includes receiving an identification of a predetermined point in a cardiac cycle of the subject and, upon identifying an occurrence of the predetermined point in the cardiac cycle, performing a saturation module configured to dephase magnetization within a region of interest (ROI) from before the predetermined point. The method also includes performing an inversion module configured to invert spins within the ROI and acquiring medical imaging data from the subject. A delay is inserted between the performance of the saturation module and the performance of the inversion module, wherein a duration of the delay is configured, with the saturation module, to control evidence in the medical imaging data of inconsistencies in the cardiac cycle of the subject by controlling a magnetization history of tissue in the ROI.

In accordance with another aspect of the present invention, a magnetic resonance imaging (MRI) system is disclosed that includes a magnet system configured to generate a polarizing magnetic field about at least a portion of a subject arranged in the MRI system and a plurality of gradient coils configured to establish at least one magnetic gradient field to the polarizing magnetic field. The MRI system also includes a radio frequency (RF) system configured to generate RF pulses and acquire medical imaging data from a subject arranged with in the MRI system and a computer system configured to control operation of the magnet system, the plurality of gradient coils, and the RF system. The computer system is configured to identify a predetermined point in a cardiac cycle of the subject and, based on the identification of the predetermined point in the cardiac cycle, control the RF system to perform a saturation module configured to dephase magnetization within a region of interest (ROI). The computer system is also configured to perform a delay between following performance of the inversion module and, after performance of the delay, control the RF system to perform an inversion module configured to invert spins within the ROI. The computer system is further configured to control the gradient coils and RF system to acquire medical imaging data. A duration of the delay is selected by the computer system, based on parameters of the saturation module, to control evidence in the medical imaging data of inconsistencies in the cardiac cycle of the subject by controlling a magnetization history of tissue in the ROI over the cardiac cycle.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
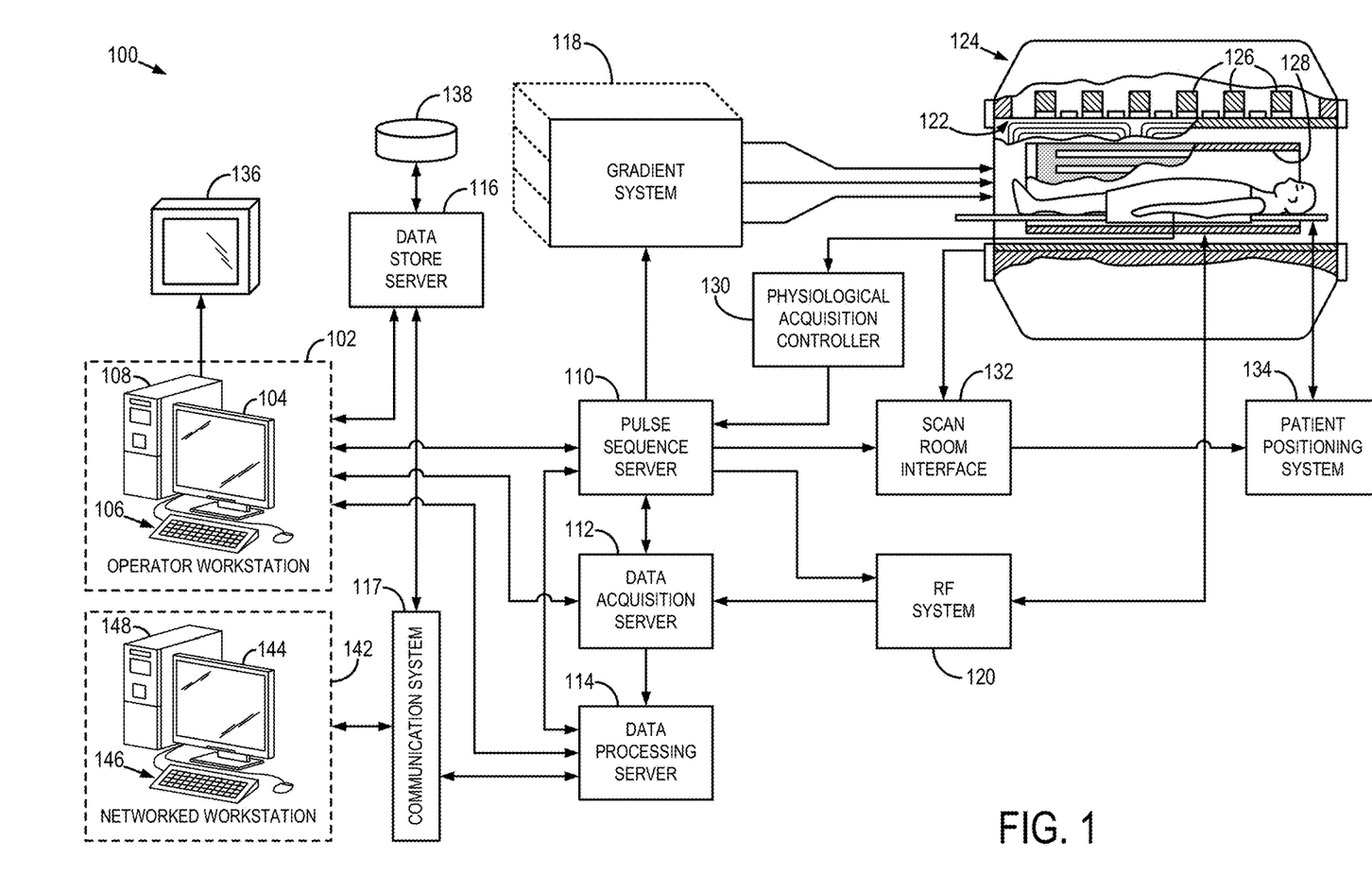
FIG. 1 is a block diagram of an exemplary MRI system configured to operate in accordance with the present invention.

Referring particularly now to FIG. 1, an example of a magnetic resonance imaging (MRI) system 100 is illustrated. The MRI system 100 includes an operator workstation 102, which will typically include a display 104, one or more input devices 106, such as a keyboard and mouse, and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 117, which may include any suitable network connection, whether wired, wireless, or a combination of both. As an example, the communication system 117 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients and used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil (not shown in FIG. 1), are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays (not shown in FIG. 1).

The RF system 120 also includes one or more RF receiver channels. Each RF receiver channel includes an RF preamplifier that amplifies the magnetic resonance signal received by the coil 128 to which it is connected, and a detector that detects and digitizes the quadrature components of the received magnetic resonance signal. The magnitude of the received magnetic resonance signal may, therefore, be determined at any sampled point by the square root of the sum of the squares of the and components:

$$M=\sqrt{I^2+Q^2}$$ Eqn. (1);

and the phase of the received magnetic resonance signal may also be determined according to the following relationship:

$$\varphi = \tan^{-1}\left(\frac{Q}{I}\right).$$ Eqn. (2)

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from respiratory bellows or other respiratory monitoring device. Such signals are typically used by the pulse sequence server 110 to synchronize, or "gate", the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography (MRA) scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 117. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

As will be described, the present invention provides a system and method for imaging that utilizes a saturation pulse added at the beginning of each heartbeat, followed by an inversion pulse after a variable delay: The saturation pulse dephases the magnetization from the previous heartbeat and the inversion pulse generates improved contrast in the T1-weighted image. This magnetization-preparation pulse sequence can be referred to as a SAturation Pulse Prepared Heart-rate independent Inversion REcovery (SAPPHIRE) pre-pulse.

Figure 2:
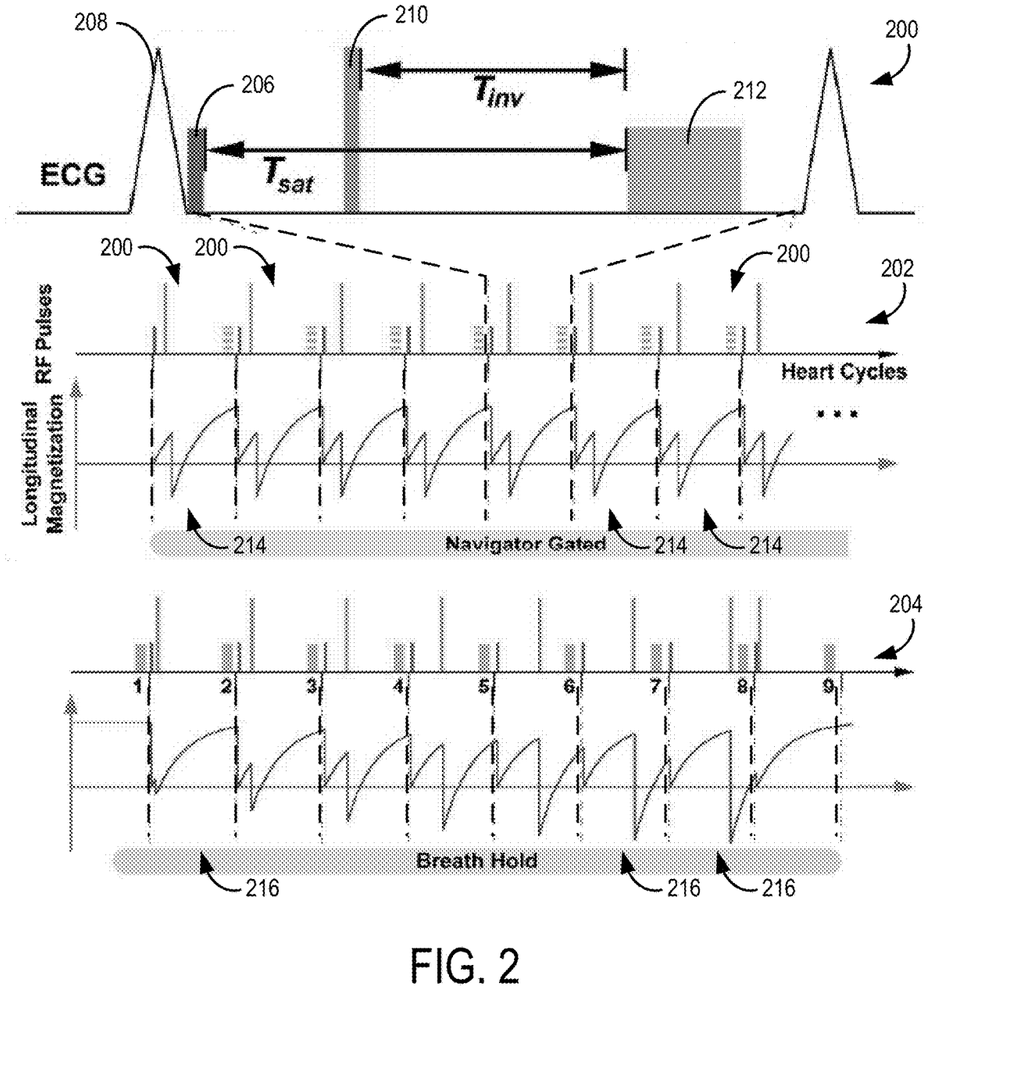
FIG. 2 is a schematic diagram and associated timing diagrams for a pulse sequence in accordance with the present invention applied to two exemplary clinical applications.

Referring to FIG. 2, a schematic diagram of a pulse sequence in accordance with the present invention includes a magnetization preparation pre-pulse or preparation module 200 that is designed to be employed within an LGE pulse sequence 202 and T1 mapping pulse sequence 204. Specifically, the pre-pulse module 200 includes a non-selective saturation pulse 206 applied based on an ECG trigger point 208, for example, immediately following an R-wave of an ECG. The saturation pulse 206 nulls the entire magnetization in the volume and erases the dependence on any preceding ECG intervals, for example, R-R intervals. A non-selective inversion pulse 210 is applied at time $T_{sat}$ less $T_{inv}$ after the saturation pulse 206, where $T_{inv}$ is the time between the inversion pulse 210 and data sampling 212, and $T_{sat}$ is the time between the saturation pulse 206 and data sampling 212.

The SAPPHIRE augmented LGE sequence 202 may be configured to be a navigator-gated 3D LGE sequence, where the SAPPHIRE pre-pulse module 200 is applied at every heartbeat 214, with the same $T_{sat}$-$T_{inv}$ times, chosen to null the healthy myocardial tissue. Characteristic signal curves 214 of the longitudinal magnetization during the application of the pulse sequence 202 are illustrated under the pulse-diagram 202.

Within the context of the LGE pulse sequence 202, the signal at time t after an inversion pulse 210 can be described with the Bloch equations as:

$$S_{LGE}(t)=M_0(1-(1+M_h)e^{-t/T1}) \quad \text{Eqn. 3;}$$

where $M_0$ is the spin-density, T1 the longitudinal relaxation time of the observed tissue, and $M_h$ is the magnetization right before the inversion and contains the information about the magnetization history. A full recovery of the magnetization in the last heartbeat corresponds to $M_h$=1. In this case a tissue with the longitudinal relaxation time T1 would be nulled T'=T1·log(2) after the inversion time.

The signal at the time t after the inversion pulse of a SAPPHIRE LGE sequence can be derived from the Bloch-equations as:

$$S_{SAPPHIRE}(t)=M_0(1-(2-e^{-(T_{sat}-T_{inv})/T1})e^{-t/T1}) \quad \text{Eqn. 4;}$$

where $M_0$ is the spin density, T1 is the longitudinal relaxation time of the observed tissue, and $T_{sat}$ and $T_{inv}$ are as defined above. If a tissue is nulled in a conventional inversion recovery sequence with full relaxation using the inversion time T', then enforcing $S_{SAPPHIRE}(T_{inv})$=0 for T1=T'/log(2) would ensure that the same tissue will be nulled using the SAPPHIRE LGE sequence. The $T_{inv}$ time of the SAPPHIRE LGE sequence can be derived from this equation, as:

$$T_{inv}(T') = T_{sat} + T'\left(1 - \frac{\log\left(e^{\log(2)T_{sat}/T'} + 1\right)}{\log(2)}\right). \quad \text{Eqn. 5}$$

Equation 5 along with the fact that the sum of $T_{sat}$ and the duration of the saturation pulse equals the cardiac trigger time, allows for the unique determination of $T_{sat}$ and $T_{inv}$ for any given T'. The inversion time conversion from Equation 5 can be integrated in the clinical scanner software such that the inversion time required for the SAPPHIRE LGE sequence is automatically calculated from the user-specified inversion time that would be typically used for a conventional LGE sequence.

Referring again to FIG. 2, the SAPPHIRE T1 mapping pulse sequence 204 can be presented as multiple 2D, single-shot image acquisitions performed with varying $T_{inv}$ to create various T1-weighted images that are used for calculation of T1 times by using a voxel-wise curve fitting to the signal intensity. Again, characteristic signal curves 216 of the longitudinal magnetization during the application of the pulse sequence 204 are illustrated under the pulse-diagram 204.

The T1 mapping pulse sequence 204 includes a number of single-shot images with SAPPHIRE pre-pulse acquired over consecutive heart beats. $T_{inv}$ is varied among the different images to create differing T1-weighted contrast. The saturation at the beginning of the heart beat removes the dependency on the magnetization history and eliminates the necessity for rest-periods. This increases the imaging efficiency. Furthermore, the freedom in choosing $T_{inv}$ enables a dense sampling of the early part of the T1 relaxation curve. Nine SAPPHIRE images can be acquired per slice in a single breath hold. Based on the anticipated maximum T1 time, inputted by the user, the effective inversion times can be linearly distributed over the applicable range. Furthermore, the pulse sequence 204 can be modified to allow for the SAPPHIRE preparation module 200 in one heart cycle, and imaging in the subsequent one to allow for longer inversion times.

In order to improve the fit conditioning, the first heart cycle can be performed without any magnetization preparation. In this case, the longitudinal magnetization is assumed to be fully recovered, allowing for the sampling of the later part of the T1 curve without prolonging the breath-hold duration.

The two-parameter model from Equation 5 can be fitted voxel-wise to the signal intensity to generate the T1 maps. The SAPPHIRE T1 mapping scheme can be used with a steady state free precision (SSFP) imaging readout due to the superior signal to noise ratio compared to, for example, gradient echo (GRE) or other suitable pulse sequences.

The above-described combination of saturation 206 and inversion pulses 210 provide an advantageous magnetization preparation for LGE and T1 mapping sequences. As will be described, measurements have shown that SAPPHIRE LGE sequence is invariant to arrhythmia and heart rate changes, and the in-vivo data indicates a robust image quality in LGE imaging for patients with arrhythmia. SAPPHIRE T1 mapping sequence is also shown to provide heart rate invariance for T1 estimation. Furthermore, it has been demonstrated that this sequence provides T1 maps of high quality in shorter breath holds compared to MOLLI and similar pulse sequences.

Specifically, the insufficient recovery after an inversion pulse in conventional LGE causes ghosting artifacts in the presence of arrhythmia and other changes in the R-R interval length. Ghosting artifacts have been shown to degrade the image quality significantly, leading to non-diagnostic images. Often they cannot be differentiated from anatomical features, or overlay with edges and make it hard to delineate compartments in the images.

Figure 3:
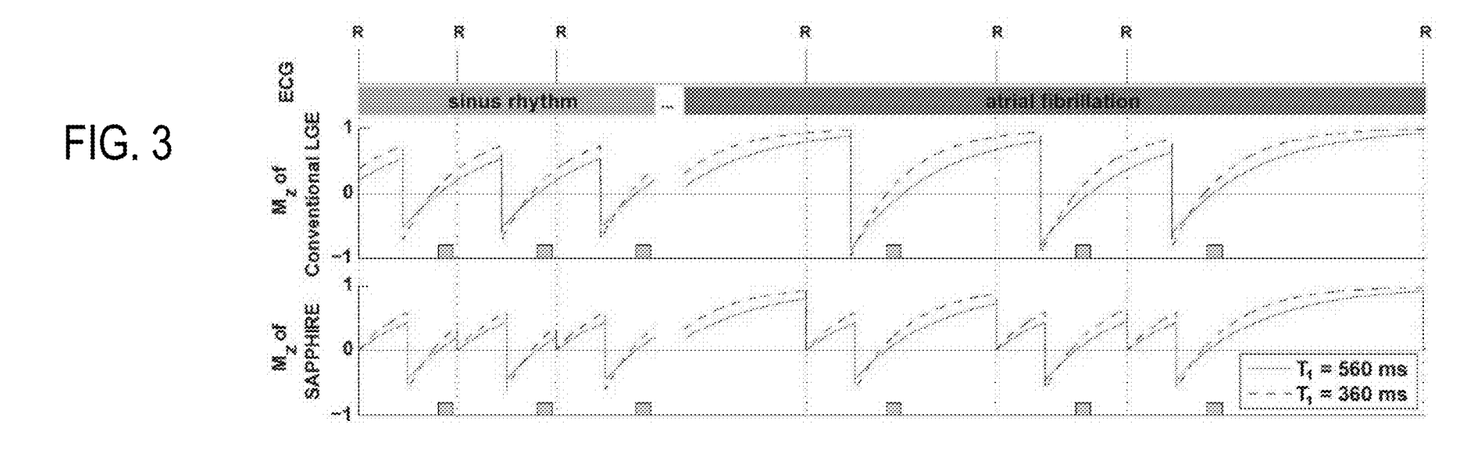
FIG. 3 is a set of graphs illustrating longitudinal magnetization (Mz) during sinus rhythm and atrial fibrillation.
Figure 4:
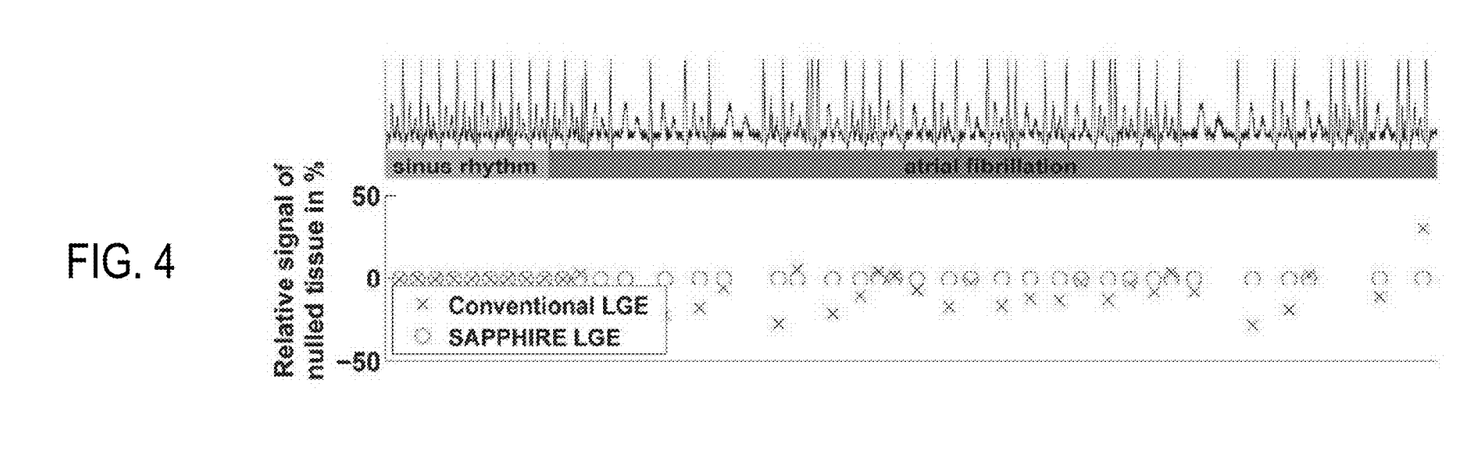
FIG. 4 is a graph illustrating that, despite the varying extent of the signal relaxation, the pulse sequence in accordance with the present invention performs consistently and traditional pulse sequence fail.

The longitudinal magnetization ($M_z$) during sinus rhythm and atrial fibrillation is depicted in FIG. 3. During sinus rhythm the magnetization relaxes to the same signal level in each heartbeat for both conventional LGE pulse sequence and SAPPHIRE LGE pulse sequence. However, in the presence of arrhythmia, the signal level right before the inversion pulse shows major variances for conventional LGE. On the other hand, the SAPPHIRE LGE pulse sequence signal right before the inversion pulse does not vary, since the magnetization history is reset using the saturation pulse. FIG. 4 shows the actual signal of the tissue that is attempted to be nulled (T1=560 ms). This indicates that, despite the varying extent of the signal relaxation, the SAPPHIRE LGE pulse sequence ensures a reliable nulling of the tissue. However, the actual signal in conventional LGE during arrhythmia deviates by up to 40 percent of the spin-density with respect to proper nulling.

Thus, the SAPPHIRE LGE pulse sequence is robust to such changes in the R-R interval length, since the addition of a saturation pulse preparation to an inversion recovery sequence negates the magnetization history at every heartbeat. Therefore, images acquired using the SAPPHIRE LGE pulse sequence, when compared to images acquired using the conventional LGE pulse sequence, are free from ghosting artifacts, which establishes the utility of the pulse sequence in patients with AF for higher quality LGE imaging.

It is contemplated that a saturation recovery, rather than an inversion recover, may be used as a pre-pulse module as way to ensure independence from the magnetization history. However, this has the inherent drawback that nulling of the healthy myocardial signal is not possible, which hampers the differentiation of scar against the myocardial background.

The SAPPHIRE LGE pulse sequence combines the advantages of the saturation recovery with the superior contrast properties of inversion recovery, providing an adequate CNR in combination with the nulling of the healthy myocardial tissue. This allows visualization similar to the conventional clinically-used LGE images.

The altered longitudinal relaxation in SAPPHIRE LGE compared to conventional LGE necessitates an explicit computation of Tinv in order to null the same tissue. This timing uniquely depends on the tissue T1 and the chosen cardiac trigger delay. In accordance with the present invention, the timing equation for the SAPPHIRE LGE sequence has been derived from the Bloch-equations that describe the T1 relaxation. In order to facilitate the clinical usage of the SAPPHIRE LGE pulse sequence, an automatic inversion time conversion has been integrated. This allows the operator to specify the inversion time as for a conventional LGE pulse sequence.

Throughout all experiments SAPPHIRE LGE resulted in a decreased CNR between the tissues of interest compared to conventional LGE. This is due to the fact that the time for recovery after the initial saturation pulse is shorter than the recovery time between two inversion pulses in the conventional LGE sequence. The amount of CNR loss depends on the relation between the heart rate and the trigger delay time. A longer trigger delay allows more recovery after the saturation pulse in the SAPPHIRE LGE sequence, but does not affect the signal of the conventional LGE in any way. Conversely, longer cardiac cycles allow for more signal regrowth after the previous inversion pulse in conventional LGE, but do not affect the SAPPHIRE LGE sequence.

In T1 mapping, the conditioning of the parameter fit determines the quality of the T1 map. The fit conditioning depends on the number of points and the time when the relaxation curve is sampled. In the MOLLI pulse sequence, the effective inversion times are determined by the R-R interval length, in such a way that only three images, corresponding to the first image of each imaging group, are acquired with inversion times shorter than the R-R interval length, while the other eight images have longer inversion times. In T1 mapping following contrast injection, where the T1 times range from 100 to 600 ms, the magnetization is largely recovered for inversion times much longer than the R-R interval length. Hence, these sample points are mostly insensitive to the actual T1 parameter and, thus, do not improve the fit conditioning for estimation of the T1 values optimally.

In SAPPHIRE T1 mapping, the inversion times can be freely chosen over the applicable range. Hence, a dense sampling of the beginning of the relaxation curve, which is highly susceptible to the T1 parameter, is enabled and yields T1 maps of higher quality. Thus, the inversion times can be linearly distributed over the applicable range. Based on the T1 values that were estimated, this translated into the preparation and the imaging being performed within the same heart cycles. For very high heart rates (>90 bpm) or estimation of longer T1 values, this scheme might be insufficient for accurate T1 mapping. In this case, imaging may be performed in the subsequent heartbeats after the application of the SAPPHIRE pre-pulse module, a feature that was already built into the pulse sequence.

In T1 mapping schemes based on the Look Locker method, the magnetization relaxation is sampled multiple times after a single preparation. Each imaging excitation induces a signal disturbance, such that a corrupted curve is sampled. At best, attempts have been made to retrospectively correct for these corruptions numerically. Since an undisturbed relaxation curve is sampled in SAPPHIRE T1 mapping there is no need for a numerical correction after the T1 parameter fit, which may account for the reduced bias in the estimated T1 times with respect to the spin echo T1 mapping sequence.

In addition to heart rate dependency, myocardial T1 mapping suffers from other challenges. Respiratory or cardiac motion will adversely impact the T1 fit, resulting in voxels with inaccurate measurements. This will impact the quantitative nature of this imaging sequence where segmental analysis of T1 is used for evaluation of diffuse fibrosis in each myocardial segment. In addition, slice profile and flip angle will directly impact the T1 measurement. Use of SSFP imaging for readout also make this imaging sequence very susceptible to various imaging artifacts which may be taken into account for increased accuracy in T1 measurements. For example, two aspects include the elimination of the sensitivity to heart rate variations and the improvement of the quality of T1 maps by an enhanced fit conditioning.

The SAPPHIRE imaging pulse sequence reduces the CNR between scar and myocardium. Studies show more homogenous T1 maps in the myocardium with less artifacts and shorter breath-hold durations.

Thus, the present invention provides a system and method for imaging referred to herein as SAPPHIRE, which combines saturation and inversion pulses and is particularly useful for LGE and T1 mapping sequences. The present invention provides improved assessment of scar and fibrosis in cardiac MRI. The saturation preparation in SAPPHIRE LGE substantially reduces the effects of changes in the R-R interval length during the scan and, thus, controls ghosting artifacts in resulting images. Therefore, the present invention enables substantially artifact-free LGE imaging in the presence of arrhythmia and heart rate variability. In SAPPHIRE T1 mapping, this preparation scheme reduces the need for rest-cycles, allowing for a shorter sequence with more homogenous T1 maps, while enabling heart rate invariant estimation of T1 values. Thus, SAPPHIRE LGE and SAPPHIRE T1 mapping sequences are potentially useful for improved depiction of scar and fibrosis, even in the presence of arrhythmia and heart rate variability.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for controlling a magnetic resonance imaging (MRI) system to acquire images of a subject having cardiac cycle inconsistencies using an overall pulse sequence performed during a cardiac cycle of the subject, the method comprising the steps of:
    receiving an identification of a predetermined point in a cardiac cycle of the subject;
    upon identifying an occurrence of the predetermined point in the cardiac cycle, performing, using a MRI system, a saturation pulse sequence configured to dephase magnetization within a region of interest (ROI) accumulated from a previous heartbeat over an interval preceding the predetermined point;
    performing, using the MRI system, an inversion pulse sequence configured to invert spins within the ROI;
    acquiring medical imaging data from the subject using the MRI system; and
    inserting a delay between the performance of the saturation pulse sequence and the performance of the inversion pulse sequence, wherein a duration of the delay is configured, with the saturation pulse sequence, to control artifacts in the medical imaging data due to cardiac cycle inconsistencies by controlling magnetization signals in the ROI.

2. The method of claim 1 further comprising performing a navigator imaging acquisition to identify the predetermined point in the cardiac cycle of the subject.

3. The method of claim 1 wherein the ROI includes a heart of the subject and the saturation pulse sequence, inversion pulse sequence, and delay are selected to null healthy myocardial tissue in the ROI.

4. The method of claim 1 wherein the inversion pulse sequence includes a non-selective inversion pulse and the delay is equal to a saturation time ($T_{sat}$) less an inversion time ($T_{inv}$), wherein $T_{sat}$ extends from completion of the saturation pulse sequence until acquiring the medical imaging data, and $T_{inv}$ extends from completion of the inversion pulse sequence until acquiring the medical imaging data.

5. The method of claim 4 wherein the saturation pulse sequence, inversion pulse sequence, and delay are repeated at each occurrence of the predetermined point in the cardiac cycle with a consistent $T_{sat}$ and $T_{inv}$.

6. The method of claim 4 wherein the overall pulse sequence includes a T1 mapping pulse sequence and the saturation pulse sequence and delay are configured to control a need for recovery periods between cardiac cycles.

7. The method of claim 4 wherein the overall pulse sequence includes a late gadolinium enhancement (LGE) pulse sequence and wherein a signal acquired when acquiring the medical imaging data at time t after the inversion pulse sequence is described by:

$$S_{LGE}(t)=M_0(1-(1+M_h)e^{-t/T1});$$

where $M_0$ is a spin-density, T1 a longitudinal relaxation time of observed tissue, $M_h$ is a magnetization of tissue immediately before performing the inversion pulse sequence and contains the information about a magnetization history of tissue in the ROI, and a full recovery of magnetization in a preceding cardiac cycle corresponds to $M_h=1$.

8. The method of claim 7 wherein the delay is selected based on an assumption that the T1 of tissue in the ROI is nulled at $T'=T1 \cdot \log(2)$ after $T_{inv}$.

9. The method of claim 7 wherein the signal at the time t after a SAturation Pulse Prepared Heart-rate Independent Inversion REcovery (SAPPHIRE) sequence is described by:

$$S_{SAPPHIRE}(t)=M_0(1-(2-e^{-(T_{sat}-T_{inv})/T1})e^{-t/T1});$$

wherein the delay is selected such that $S_{SAPPHIRE}(T_{inv})=0$ for T1 $=T'/\log(2)$.

10. The method of claim 7 wherein $T_{inv}$ is described by:

$$T_{inv}(T') = T_{sat} + T'\left(1 - \frac{\log\left(e^{\log(2)T_{sat}/T'} + 1\right)}{\log(2)}\right).$$

11. A magnetic resonance imaging (MRI) system, comprising:
    a magnet system configured to generate a polarizing magnetic field about at least a portion of a subject arranged in the MRI system;
    a plurality of gradient coils configured to establish at least one magnetic gradient field to the polarizing magnetic field;
    a radio frequency (RF) system configured to generate RF pulses and acquire medical imaging data from a subject arranged with in the MRI system by performing an overall pulse sequence during a cardiac cycle of the subject;
    a computer system configured to control operation of the magnet system, the plurality of gradient coils, and the RF system to:
        identify of a predetermined point in the cardiac cycle of the subject;
        based on the identification of the predetermined point in the cardiac cycle, control the RF system to perform a saturation pulse sequence configured to dephase magnetization within a region of interest (ROI) accumulated from a previous heartbeat over an interval preceding the predetermined point;
        perform a delay between following performance of the inversion pulse sequence;
        after performance of the delay, control the RF system to perform an inversion pulse sequence configured to invert spins within the ROI;
        control the gradient coils and RF system to acquire medical imaging data from the ROI; and
        wherein a duration of the delay is selected, based on parameters of the saturation pulse sequence, to control artifacts in the medical imaging data due to cardiac cycle inconsistencies by controlling magnetization signals in the ROI over the cardiac cycle.

12. The system of claim 11 wherein the computer system is further configured to perform a navigator imaging acquisition to identify the predetermined point in the cardiac cycle of the subject.

13. The system of claim 11 wherein the overall pulse sequence includes a T1 mapping pulse sequence and the saturation pulse sequence and delay are configured to control a need for recovery periods between cardiac cycles.

14. The system of claim 11 wherein the ROI includes a heart of the subject and the saturation pulse sequence, inversion pulse sequence, and delay are selected to null healthy myocardial tissue in the ROI.

15. The system of claim 11 wherein the inversion pulse sequence includes a non-selective inversion pulse and the delay is equal to a saturation time ($T_{sat}$) less an inversion time ($T_{inv}$), wherein $T_{sat}$ extends from completion of the saturation pulse sequence until acquiring the medical imaging data, and $T_{inv}$ extends from completion of the inversion pulse sequence until acquiring the medical imaging data.

16. The system of claim 15 wherein the saturation pulse sequence, inversion pulse sequence, and delay are repeated at each occurrence of the predetermined point in the cardiac cycle with a consistent $T_{sat}$ and $T_{inv}$.

17. The system of claim 15 wherein $T_{inv}$ is described by:

$$T_{inv}(T') = T_{sat} + T'\left(1 - \frac{\log\left(e^{\log(2)T_{sat}/T'} + 1\right)}{\log(2)}\right).$$

18. The system of claim 15 wherein the overall pulse sequence includes a late gadolinium enhancement (LGE) pulse sequence and wherein a signal acquired when acquiring the medical imaging data at time t after the inversion pulse sequence is described by:

$$S_{LGE}(t) = M_0(1 - (1+M_h)e^{-t/T1});$$

where $M_0$ is a spin-density, T1 a longitudinal relaxation time of observed tissue, $M_h$ is a magnetization of tissue immediately before performing the inversion pulse sequence and contains the information about a magnetization history of tissue in the ROI, and a full recovery of magnetization in a preceding cardiac cycle corresponds to $M_h=1$.

19. The system of claim 18 wherein the computer system is configured to select the delay based on an assumption that the T1 of tissue in the ROI is nulled at $T'=T1 \cdot \log(2)$ after the $T_{inv}$.

20. The system of claim 18 wherein the signal at the time t after a SAturation Pulse Prepared Heart-rate Independent Inversion REcovery (SAPPHIRE) sequence is described by:

$$S_{SAPPHIRE}(t) = M_0(1 - (2 - e^{-(T_{sat}-T_{inv})/T1})e^{-t/T1});$$

wherein the delay is selected such that $S_{SAPPHIRE}(T_{inv}) = 0$ for T1=T'/log(2).

* * * * *